United States Patent [19]

Armstrong et al.

[11] Patent Number: 4,720,457
[45] Date of Patent: Jan. 19, 1988

[54] SELECTIVE PRODUCTION OF ETHYL ACETATE AND ACETALDEHYDE BY MICROORGANISMS

[75] Inventors: David W. Armstrong; Stanley M. Martin, both of Ottawa; Hiroshi Yamazaki, Nepean, all of Canada

[73] Assignee: Canadian Patents and Development Ltd., Ottawa, Canada

[21] Appl. No.: 873,826

[22] Filed: Jun. 9, 1986

Related U.S. Application Data

[63] Continuation of Ser. No. 684,109, Dec. 20, 1984, abandoned.

[51] Int. Cl.$^4$ .......................... C12P 7/62; C12P 7/24
[52] U.S. Cl. ..................................... 435/135; 435/147
[58] Field of Search ............................... 435/135, 147

Primary Examiner—Leonard Schenkman
Assistant Examiner—Joseph A. Lipovsky
Attorney, Agent, or Firm—Alan A. Thomson

[57] ABSTRACT

This invention is concerned with the selective production of ethyl acetate and acetaldehyde by microorganisms, for example of the genus Candida and of the genus Hansenula. Ethyl acetate or acetaldehyde may be produced by altering the concentration of ethanol in the medium.

10 Claims, 1 Drawing Figure

SELECTIVE PRODUCTION OF ETHYL ACETATE AND ACETALDEHYDE BY MICROORGANISMS

This application is a continuation of application Ser. No. 684,109, filed 12-20-84, now abandoned.

BACKGROUND TO THE INVENTION

Both ethyl acetate and acetaldehyde are feedstock chemicals of some economic importance. There are many sources of dilute ethanol wastes such as the brewing industry, biomass conversion processes and processes for fermenting cellulose and hemicellulose currently under consideration. Economical recovery of these ethanol wastes by, for example direct extractive fermentation, selective membrane fermentation, vacuum fermentation, adsorption/desorption, electrochemical oxidation or in the form of valuable chemicals such as ethyl acetate and acetaldehyde, is of interest. T. M. Meshbesher, in U.S. Pat. No. 4,347,109, describes an electrochemical method for making acetaldehyde from ethanol. D. W. Armstrong et al, in Biotechnol. Bioeng. 25, 2567–2575, 1984, have shown that dilute ethanol can be converted to ethyl acetate by *Candida utilis* but that higher concentrations of ethanol were strongly inhibitory (both dilute and higher concentrations of ethanol being less than 10%). The production of acetaldehyde from such microorganisms and an ability to switch, at will, from the production of acetaldehyde to ethyl acetate and vice versa, may prove useful especially where dilute alcoholic wastes are produced and provide means for conveniently switching from the production of one compound to the other as desired.

SUMMARY OF THE INVENTION

This invention is concerned with methods of producing acetaldehyde comprising biological oxidation of ethanol with at least one organism selected from species of the genera Candida and Hansenula capable of such biological oxidation, under conditions substantially free of dissolved iron, wherein the ethanol concentration is maintained above about 35 g/L, preferably at about 65 g/L. The pH is preferably maintained between 2 and 8, preferably at about 7, and the temperature is preferably above about 21° C. An additional step comprising collecting evaporated acetaldehyde may be employed.

Particular embodiments of the invention comprises the biological oxidation of ethanol with *Candida utilis* or a yeast of the type *Hansenula anomala* ATCC 2102 in minimal salts medium substantially free of dissolved iron at a pH of about 7, a temperature of about 28° C. and with the ethanol concentration maintained at about 65 g/L.

This invention is further concerned with methods of switching between the production of acetaldehyde and the production of ethyl acetate comprising the biological oxidation of ethanol with at least one organism selected from species of the genera Candida and Hansenula capable of such biological oxidation, under conditions substantially free of dissolved iron, wherein to switch from acetaldehyde production to ethyl acetate production the concentration of ethanol is reduced to below about 35 g/L and to switch from ethyl acetate production to acetaldehyde production the concentration of ethanol is raised to above about 35 g/L.

DETAILED DESCRIPTION

Figure 1:
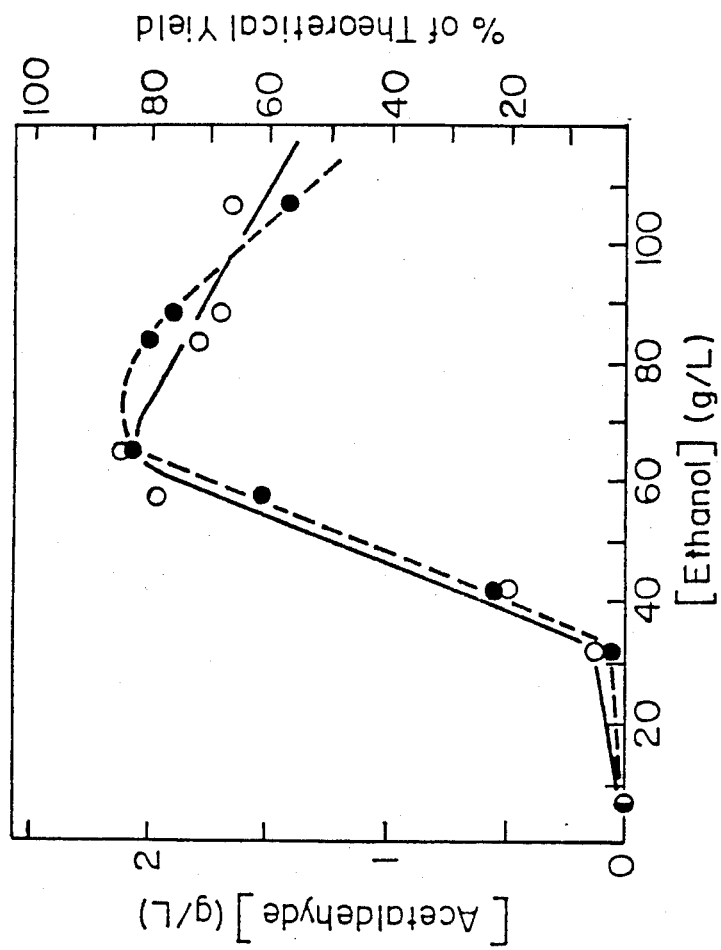
FIG. 1 shows the effect of ethanol concentration on acetaldehyde accumulation and yield. Ethanol adapted *Candida utilis* cells were resuspended to $A_{620}=2.0$ in nitrogen-free medium (pH 7.0) containing different levels of ethanol and incubated for 5 hr. Theoretical yields of acetaldehyde were based on the conversion of 1 mole of ethanol to 1 mole acetaldehyde. Solid circles and the dotted line indicate acetaldehyde accumulation. Open circles and the continuous line indicate acetaldehyde yield.

*Candida utilis* NRC 2721 (NRRL Y-900, ATCC 9950) was grown in a minimal salts medium of K. C. Thomas and P. S. S. Dawson, Can. J. Microbiol. 24, 440, 1978, without ferric chloride supplementation. Cultures were incubated at 28° C. with shaking at 150 rpm in closed flasks having a head space/culture volume ratio of about 5.0. Cell mass density was measured by absorbance at 620 nm ($A_{620}$).

The cells were acclimatized by being grown overnight ($A_{620}=1.0$) in the medium containing 10 g/L ethanol and were harvested by centrifugation at 3500 g. The cells were washed by resuspension and centrifugation, and resuspended in the ethanol-containing medium.

All volatile products were confirmed by gas chromatography-mass spectrometry and routinely assayed by gas chromatography.

It has been previously shown that the rate of conversion of ethanol to ethyl acetate by *C. utilis* increased with ethanol concentration up to about 10 g/L and then gradually declined to zero when the substrate concentration reaches about 35 g/L by D. W. Armstrong et al, op. cit. We have now found that at ethanol concentrations higher than 35 g/L, significant amounts of acetaldehyde accumulated in a *C. utilis* culture whereas ethyl acetate was predominant at the initial concentration of 10 g/L. Although the initial ethanol concentrations from 10 g/L to 43 g/L did not affect the rate of ethanol utilization, the profile of product accumulation differed markedly. The initial ethanol concentration—of about 35 g/L allowed transient accumulation of acetaldehyde until the ethanol concentration declined to about 32 g/L, below which acetic acid and ethyl acetate accumulated as acetaldehyde declined. At the initial ethanol concentration of 43 g/L, acetaldehyde accumulated before acetic acid and ethyl acetate was not detected.

The above experiments were performed at an initial pH of 6. Ethyl acetate accumulation in *C. utilis* is optimal between 6 and 7. To obtain the optimal pH for acetaldehyde accumulation, ethanol-adapted *C. utilis* cells were incubated at various pH at the initial ethanol concentration of 65 g/L. The nitrogen source, ammonium sulfate, was omitted to prevent a net increase in cell protein to allow comparison of acetaldehyde productivity per unit of cell protein. Table 1 shows that the initial pH of 7 allowed optimal acetaldehyde accumulation.

FIG. 1 shows the effect of different ethanol levels on accumulation and yield of acetaldehyde after 5 hr incubation. Acetaldehyde accumulation was negligible up to ethanol concentrations of about 35 g/L. Both accumulation and yield of acetaldehyde increased with higher ethanol concentrations up to about 65 g/L, above which they declined gradually. Theoretical yields of acetaldehyde greater than 50% were obtained at initial ethanol concentrations from 50 to 110 g/L. Based on the results presented it should be possible to obtain yields higher than 80% if ethanol were continuously fed to maintain a level of about 65 g/L.

The present results were obtained with cells suspended in medium in sealed containers (closed systems). It was noted that acetaldehyde may be further oxidized to acetic acid and preliminary experiments in an open system have indicated that the continuous removal of acetaldehyde minimizes accumulation of acetic acid which in turn prevents a drop in pH to levels found to be less optimal for acetaldehyde accumulation (Table 1). A fermentor system to allow continuous feeding of ethanol and simultaneous low energy evaporation of acetaldehyde is being constructed as an embodiment of the invention likely to be exploited on a large scale.

The presence of dissolved iron severely inhibits ethanol utilization but may be countered by increased aeration, within limits. Very high rates of aeration have been found to be detrimental to ethyl acetate

TABLE 1

Effect of pH on Acetaldehyde Accumulation

| Initial pH | Percent of maximum acetaldehyde accumulation | |
|---|---|---|
| | 5 hr | 24 hr |
| 3.1 | 43 (3.2) | 43 (3.2) |
| 4.0 | 55 (3.7) | 43 (3.7) |
| 5.8 | 61 (4.9) | 63 (4.3) |
| 7.0 | 100 (6.7) | 100 (6.1) |
| 7.3 | 51 (7.0) | 99 (6.7) |
| 7.6 | 60 (7.2) | 84 (7.0) |

The medium containing 15 g/L $KH_2PO_4$ was adjusted to different pH with HCl or NaOH. Ethanol-adapted *C. utilis* cells were resuspended to $A_{620}$ = 2.0 in the medium containing 65 g/L ethanol and no ammonium sulfate and incubated for 5 and 24 hr.
Maximum acetaldehyde accumulation occurred at an initial pH of 7.0 and was 3.5 g/L at both 5 hr and 24 hr.
Numbers in brackets represent pH at time of sampling accumulation (D. W. Armstrong et al, Canadian Society of Microbiologists, Abstract, June 1983).

The yeast *Hansensula anomala* (ATCC 2102) has been studied under similar conditions to those used in the study of *Candida utilis* and was shown to produce about 15% of theoretical yield (weight basis) from ethanol in 24 hours.

The above results, demonstrating the production of acetaldehyde, when taken in conjunction with the results demonstrating the production of ethyl acetate given in D. W. Armstrong et al (op. cit.), indicate that such systems would offer the opportunity of being able to switch between the production of acetaldehyde and ethyl acetate by simply manipulating and controlling the concentration of ethanol in the medium. Reducing the concentration of ethanol from above about 35 g/L to below about 35 g/L, allows one to switch from the production of acetaldehyde to the production of ethyl acetate. Increasing the concentration of ethanol from below about 35 g/L to above about 35 g/L allows one to switch from the production of ethyl acetate to the production of acetaldehyde.

We claim:

1. A method of producing acetaldehyde comprising:
(a) inoculating an ethanol containing aqueous medium with ethanol-acclimatized cells of an organism selected from *Candida utilis* ATCC 9950, *Hansenula anomala* ATCC 2102 and strains of said organisms possessing similar oxidation characteristics; and
(b) fermenting said medium resulting from step (a) at a pH between 2 and 8 with the provisos that ethanol concentration is maintained above 35 g/L and up to approximately 65 g/L and conditions are maintained substantially free of dissolved iron and at temperatures from about 21° C. up to that known to support viability of the organism to yield acetaldehyde.

2. The method of claim 1 wherein the organism is selected from the group consisting of *Candida utilis* ATCC 9950 and *Hansenula anomala* ATCC 2102.

3. The method of claim 1 wherein the pH of the medium is maintained at about 7.

4. The method of claim 1 wherein the ethanol concentration is maintained at about 65 g/L.

5. The method of claim 1 wherein the temperature is maintained above about 21° C.

6. The method of claim 1 with an additional step comprising collecting evaporated acetaldehyde.

7. The method of claim 1 wherein the organism is of the *Candida utilis* ATCC 9950 type and step (b) comprises fermenting the medium with minimal salts substantially free of dissolved iron at a pH of about 7, a temperature of about 28° C. and an ethanol concentration maintained at about 65 g/L.

8. The method of claim 1 wherein the organism is of the *Hansenula anomala* ATCC 2102 type and step (b) comprises fermenting the medium with minimal salts substantially free of dissolved iron at a pH of about 7, a temperature of about 28° C. and an ethanol concentration maintained at about 65 g/L.

9. A method of switching between the production of acetaldehyde and the production of ethyl acetate in the same fermentation comprising:
(a) inoculating an ethanol containing aqueous medium with at least one organism selected from *Candida utilis* ATCC 9950, *Hansenula anomala* ATCC 2102 and strains of said organisms possessing similar oxidation characteristics;
(b) fermenting said medium under conditions substantially free of dissolved iron at a pH of about 7, and at temperatures from about 21° C. up to that known to support viability of the organism, and
(c) switching from acetaldehyde production to ethyl acetate production by reducing the concentration of ethanol to below about 35 g/L or from ethyl acetate production to acetaldehyde production by raising the concentration of ethanol to above about 35 g/L.

10. The method of claim 9 wherein the organism is selected from the group consisting of *Candida utilis* ATCC 9950 and *Hansenula anomala* ATCC 2102.

* * * * *